(12) United States Patent
Kususawa et al.

(10) Patent No.: US 6,219,476 B1
(45) Date of Patent: Apr. 17, 2001

(54) MULTIPLE LIGHT SOURCE UNIT AND OPTICAL SYSTEM USING THE SAME

(75) Inventors: Hideo Kususawa; Yasuyuki Imura, both of Kobe; Masaki Ishisaka, Himeji, all of (JP)

(73) Assignee: Sysmex Corporation, Hyogo (JP)

( * ) Notice: Subject to any disclaimer, the term of this patent is extended or adjusted under 35 U.S.C. 154(b) by 0 days.

(21) Appl. No.: 09/369,314

(22) Filed: Aug. 6, 1999

(30) Foreign Application Priority Data

Aug. 7, 1998 (JP) .................................................. 10-224601

(51) Int. Cl.$^7$ ...................................................... G02B 6/32
(52) U.S. Cl. .................. 385/33; 385/31; 385/92; 385/93; 359/618
(58) Field of Search ..................... 385/33–35, 31, 385/47, 49, 15, 24, 88–94; 359/618, 629, 639; 362/574; 356/335

(56) References Cited

U.S. PATENT DOCUMENTS 4,284,355 * 8/1981 Hansen et al. ........................ 356/335
6,075,912 * 6/2000 Goodman .............................. 385/33

FOREIGN PATENT DOCUMENTS 56-67756    6/1981 (JP) ...................................... 356/335

* cited by examiner

Primary Examiner—Phan T. H. Palmer

(57) ABSTRACT

A multiple light source unit includes a plurality of light sources for emitting light beams. There is a condensing lens and the light beams are parallel to an optical axis of the condensing lens. Included is a mirror for directing the light beams from the plurality of light sources to the condensing lens. A light guiding element for receiving the condensed light beams through a light receiving section and for emitting the light beams through a light emitting section is also provided. The light beams from the plurality of light sources are incident, through respective positions on the condensing lens, into the light receiving section of the light guiding element.

15 Claims, 12 Drawing Sheets

MULTIPLE LIGHT SOURCE UNIT AND OPTICAL SYSTEM USING THE SAME

CROSS REFERENCES TO RELATED APPLICATIONS

This application is related to Japanese patent application No. HEI 10(1998)-224601 filed on Aug. 7, 1998 whose priority is claimed under 35 USC §119, the disclosure of which is incorporated herein by reference in its entirety.

BACKGROUND OF THE INVENTION

1. Field of the Invention

The present invention relates to a multiple light source unit and an optical system using the same, and more particularly to a light source apparatus for converting light beams emitted from a plurality of light sources into a single light beam to be emitted from a specific position. For example, the multiple light source unit is used in a particle analyzing apparatus for radiating light onto a particle flowing in a fluid for detection of its scattered light or transmitted light and for capturing an image of the particle.

2. Description of the Related Art

A conventional multiple light source apparatus is known in which light beams emitted from a plurality of laser light sources are converted into light beams having a common optical axis by means of a half mirror (See, for example, Japanese Unexamined Patent Publication No. SHO 56(1981)-67756).

However, such a conventional light source apparatus lacks compactness and also requires a cumbersome adjustment. Moreover, loss of light due to the half mirror is inevitable. Further, if an image is captured using laser light, there are generated interference fringes, Fresnel diffraction, Fraunhofer diffraction, and the like due to coherence of the laser light with respect to space and time, thereby degrading an image quality.

On the other hand, the properties required in a light source are as follows:

(A) High uniformity of radiation intensity,
(B) High electro-optical energy-conversion efficiency,
(C) Small size and small weight,
(D) Facility in handling emitted light, and
(E) High output stability and less change with time.

However, these properties are contradictory to each other as shown below.

(A) High uniformity of radiation intensity

A high uniformity of radiation intensity in a field of view means that the coherence is sufficiently low. Therefore, the high uniformity in the radiation light intensity cannot be obtained unless a light beam of a specific angle emitted from a light source having a sufficiently low coherence is used.

(B) High electro-optical energy conversion efficiency

A light source having a high energy-conversion efficiency means a light source having a high coherence. This is contradictory to the property of (A). The reason is that uniformity in the radiation light intensity cannot be obtained unless a light source having a sufficiently low coherence, i.e. a light source having a low electro-optical conversion efficiency, is used.

Moreover, the fact that only a specific light beam from the light source can be used further decreases the conversion efficiency. The electro-optical conversion efficiency of a halogen lamp, a xenon lamp, or a flash lamp to be used as a microscope light source is typically several percent, and the amount of light actually used for capturing images is less than 1%. On the other hand, it is well known in the art that a coherent light source such as represented by a semiconductor laser has a conversion efficiency of 10 to 40%. However, if a light source having a high coherence is used as a light source for capturing images, it is not possible to obtain a clear image due to an influence of diffraction, interference, speckles, or the like.

(C) Small size and small weight

A small size means use of a coherence light source having a high electro-optical energy-conversion efficiency shown in (B). However, this is contradictory to the property of (A). Moreover, it is necessary to compactly arrange optical elements including light source elements and coherence reducing elements, without creating a dead space.

(D) Facility in handling emitted light

This means that the light source has a precise optical axis to be handled with high precision. Therefore, it is necessary that all the light beams from the light source are concentrated within a specific angle range.

(E) High output stability and less change with time

High output stability and less change with time mean adoption of a small and thermally stable structure having a high electro-optical conversion efficiency.

Therefore, light sources including a laser and an SLD can satisfy the items (B), (C), and (D), but not the item (A); whereas incandescent light sources can satisfy the property (A) under limited conditions, but not the other items.

SUMMARY OF THE INVENTION

The present invention has been made in view of these circumstances and the purpose thereof is to provide a small multiple light source unit capable of effectively converting light beams from a plurality of light sources into a single light beam.

The present invention provides a multiple light source unit comprising: a plurality of light sources for emitting light beams; a condensing lens, the light beams being parallel to an optical axis of the condensing lens; a mirror for directing the light beams from the plurality of light sources to the condensing lens; and a light guiding element for receiving the condensed light beams through a light receiving section and for emitting the light beams through a light emitting section, wherein the light beams from the plurality of light sources are incident, through respective positions on the condensing lens, into the light receiving section of the light guiding element.

According to another aspect, the present invention provides a multiple light source unit in which the above-mentioned mirror and the condensing lens are replaced with a single mirror having the same function, for example a concave mirror.

According to still another aspect, the present invention provides an optical system for performing dark field illumination on an object by using the above-mentioned multiple light source unit, so as to capture an image of the object clearly.

BRIEF DESCRIPTION OF THE DRAWINGS

The present invention will be better understood from the following detailed description of preferred embodiments of the invention, taken in conjunction with the accompanying drawings, in which.

DETAILED DESCRIPTION OF THE PREFERRED EMBODIMENTS

Figure 1:
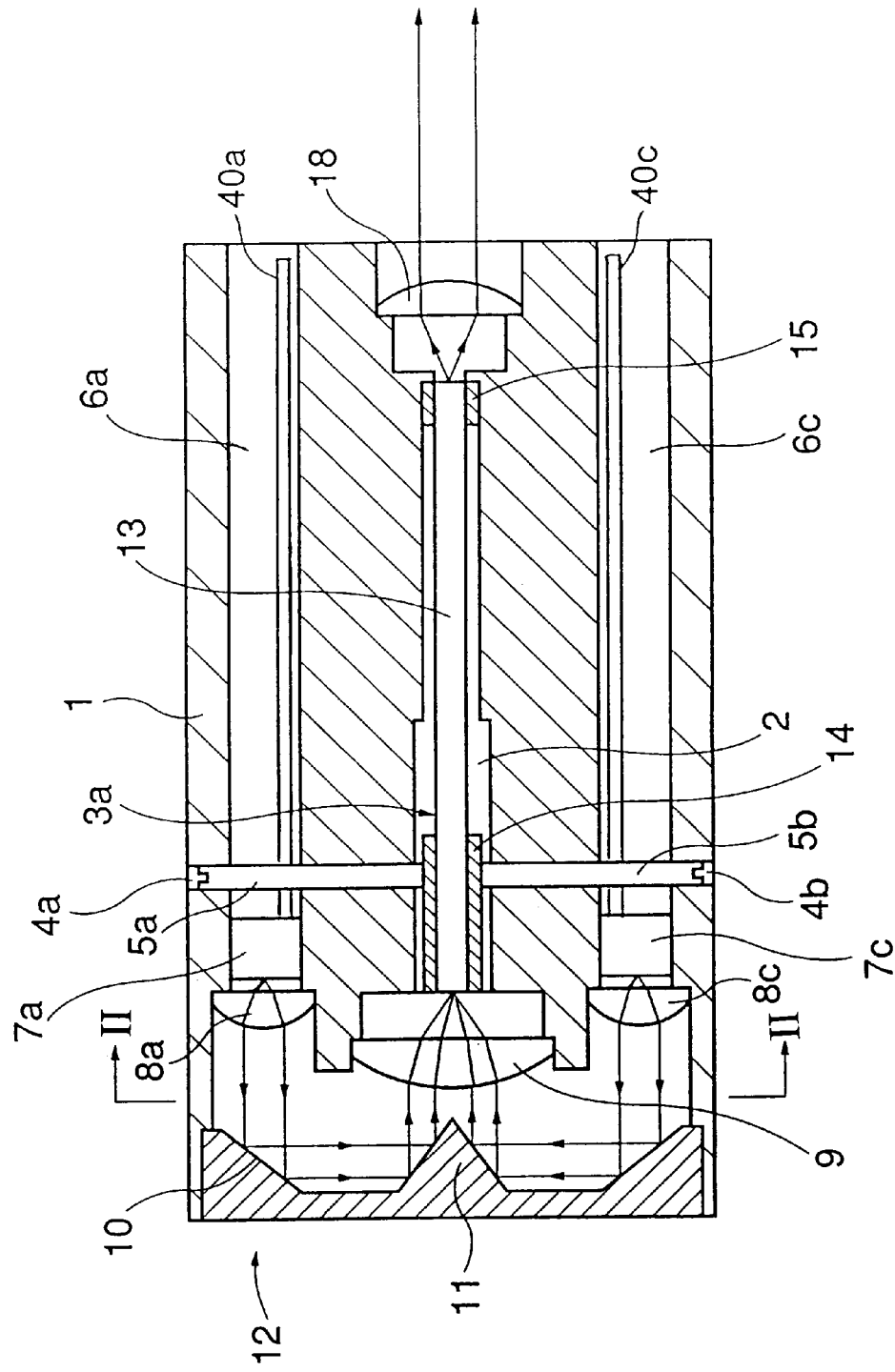
FIG. 1 is a cross-sectional view showing a construction of a first embodiment of a multiple light source unit according to the present invention.

The plurality of light sources according to the present invention may be a combination of a coherence light source such as a pulse laser or a continuous-light laser, with a non-coherence light source such as an LED in accordance with an intended use. These light sources may include a collimator lens for emitting a collimated light beam. The plurality of light sources may emit light selectively or simultaneously in accordance with an intended purpose. The plurality of light sources may be replaced with a single light source and may be selectively turned on.

In the present invention, for the purpose of achieving compactness, the plurality of light sources are preferably spaced apart on a circumference coaxial with an optical axis of the condensing lens.

It is possible to adopt a construction in which the plurality of light sources are spaced apart on a circumference coaxial with an optical axis of the condensing lens; the mirror comprises a first mirror and a second mirror, the first mirror reflecting the light beams from the light sources in a direction that intersects the optical axis of the condensing lens, the second mirror allowing the light beams reflected from the first mirror to be incident into the condensing lens by directing the light beams in a direction parallel to the optical axis of the condensing lens.

Thus, an effective spatial arrangement is made possible by arranging the light sources near to each other on a circumference with respect to the optical axis of the condensing lens.

The first mirror may be a conical internal-reflection mirror for reflecting the light beams from the plurality of light sources, and the second mirror may be a conical external-reflection mirror for reflecting the light beams from the first mirror.

The conical external-reflection mirror may be configured to allow the light beam incident into a bottom thereof to be emitted from an apex thereof.

The plurality of light sources are preferably arranged in such a manner that the optical paths from the light sources to the condensing lens are equal to each other in length. If the optical path lengths from the light sources to the condensing lens are equal to each other, the changes caused by thermal expansion in the optical paths from the light sources to the condensing lens will be equal to each other and the light condensing ratio of the light beam from each light source changes uniformly. This means that the convergence ratio of a light beam from a particular one of the plurality of the light sources does not change to an extreme extent, thereby improving the stability of the light beams incident into the light guiding element.

In the present invention, the light guiding element may include a coherence reducing element for reducing the coherence of the incident light beam. If one or more light beams are incident into the coherence reducing element, the coherence reducing element mixes these light beams and reduces their coherence to flatten the light intensity distribution. The coherence reducing element may be a wave front converting element, an optical phase modulating element, or a combination thereof. Accordingly, the coherence reducing element may be a multi-mode optical fiber (a large-aperture optical fiber manufactured by Sumitomo Electric Industries, Ltd.), which is a wave front converting element.

Here, it is preferable to bend the multi-mode optical fiber locally into a W-shape in order to reduce the coherence of the light beam more effectively. This is because the bending of the multi-mode optical fiber generates a non-stationary propagation mode other than the stationary propagation modes of the optical fiber, whereby the light intensity distribution is further flattened. However, the W-shaped bent portion is preferably disposed near the light-emitting end of the optical fiber so as not to damp the non-stationary propagation mode light.

Alternatively, the coherence reducing element may be constructed with two multi-mode optical fibers and an optical diffusing/scattering member inserted therebetween. The optical diffusing/scattering member may be, for example, a holographic diffusing plate (which may be a diffusing film), a homogenizer, or the like. In this case, the inserted optical diffusing/scattering member further flattens the light intensity distribution in the same manner as the above-mentioned W-shaped bend portion. The number of propagation modes may be further increased by using the optical diffusing/scattering member.

Still alternatively, the coherence reducing element may be constructed with a series connection of a multi-mode optical fiber, an optical diffusing/scattering member, and a metal pipe with a optically polished inner surface. In this case, the metal pipe acts as an optical guide path for guiding a non-stationary propagation mode wave. The metal pipe having the polished inner surface may further divide and split the propagation mode wave to increase its number by fine irregularities present in the inner surface and having a size of the optical wavelength or less.

If an optical phase modulating element is to be used as the coherence reducing element, it is possible to use an element obtained by disposing an electro-optical crystal (also referred to as non-linear crystal) such as $LiNbO_3$, $LiTaO_3$, or $TeO_2$ in a microwave resonator. The optical phase modulating element may be, for example, "Bulk Electro-optic modulator 4841" manufactured by New Focus, Inc.

This phase modulating element allows a laser beam to be transmitted through an electro-optical crystal and allows a microwave to be input into a microwave resonator by using an external driving means, whereby the spectrum width of the laser transmitted through the electro-optical crystal is broadened to reduce the coherence with respect to time.

In the present invention, the light diffusing/scattering element is preferably one of a holographic diffusing plate, a holographic diffusing film, and a homogenizer. The holographic diffusing plate, the holographic diffusing film, and the homogenizer basically have irregularities equivalent to an optical wavelength or less, so that the propagation mode of light can be divided and split without generation of diffraction or the like.

Further, the coherence reducing element preferably includes a light-receiving aperture disposed facing the condensing lens for receiving a light beam from the condensing lens. Preferably, the incident angles of the light beams directed to the light-receiving section from the condensing lens are set to be smaller than the maximum incident angle defined by the numerical aperture of the light-receiving section. This may prevent loss of light.

Also, in the present invention, a single mirror may be used instead of the first mirror, the second mirror, and the condensing lens. In other words, the present invention further provides a multiple light source unit comprising: a plurality of light sources for emitting light beams; a single mirror for reflecting and condensing the light beams from the plurality of light sources; and a light guiding element for receiving the condensed light beams through a light receiving section and for emitting the light beams through a light emitting section, wherein the light beams from the plurality of light sources are incident, through respective positions on the single mirror, into the light receiving section of the light guiding element. The single mirror may be a concave mirror.

In this case, the plurality of light sources may include a laser light source and the light guiding element may include a coherence reducing element for reducing a coherence of the received light beams.

Also, it is preferable that the plurality of light sources are spaced apart on a circumference coaxial with the optical axis of the concave mirror; the light guiding element has an optical axis that coincides with the optical axis of the concave mirror; and the light receiving aperture is positioned at a focal point of the concave mirror.

Hereafter, the present invention will be explained in detail with reference to embodiments thereof shown in the attached drawings. However, the present invention is in no way intended to be limited by these embodiments and drawings.

FIRST EXAMPLE

Figure 2:
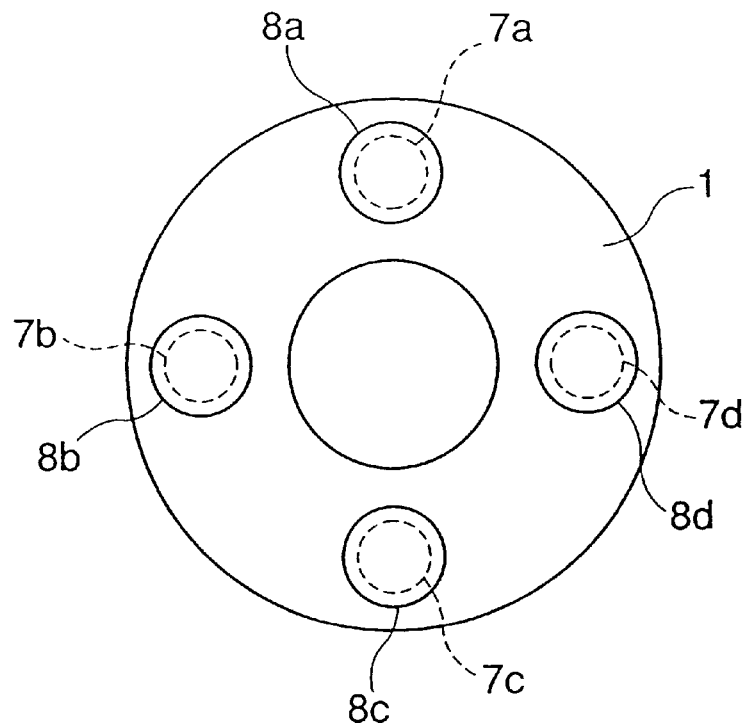
FIG. 2 is a cross-sectional view cut along an II-II line of FIG. 1.

FIG. 1 is a cross-sectional view showing a construction of a first embodiment of a multiple light source unit according to the present invention. FIG. 2 is a cross-sectional view cut along an II-II line of FIG. 1.

In these views, a coherence reducing element 3a is inserted in a through-bore 2 disposed coaxially with the central axis of a cylindrical main body 1. The tip end of the coherence reducing element 3a is fixed onto an inner wall of the through-bore 2, and the rear end of the coherence reducing element 3a is fixed by threads 5a, 5b inserted respectively into threadholes 4a, 4b formed perpendicular to the central axis of the main body 1.

Further, in the main body 1, four through-bores 6a, 6b, 6c, 6d (6b, 6d are not shown) parallel to the through-bore 2 are spaced apart on a circumference coaxial with the central axis of the main body 1. Light sources 7a, 7b, 7c, 7d and collimator lenses 8a, 8b, 8c, 8d are disposed at the tip ends of the four through-bores 6a, 6b, 6c, 6d, respectively (See FIG. 2).

Also, circuit boards 40a, 40b, 40c, 40d (40b, 40d are not shown) for driving the light sources are disposed in the insides of the through-bores 6a, 6b, 6c, 6d, respectively.

Figure 3:
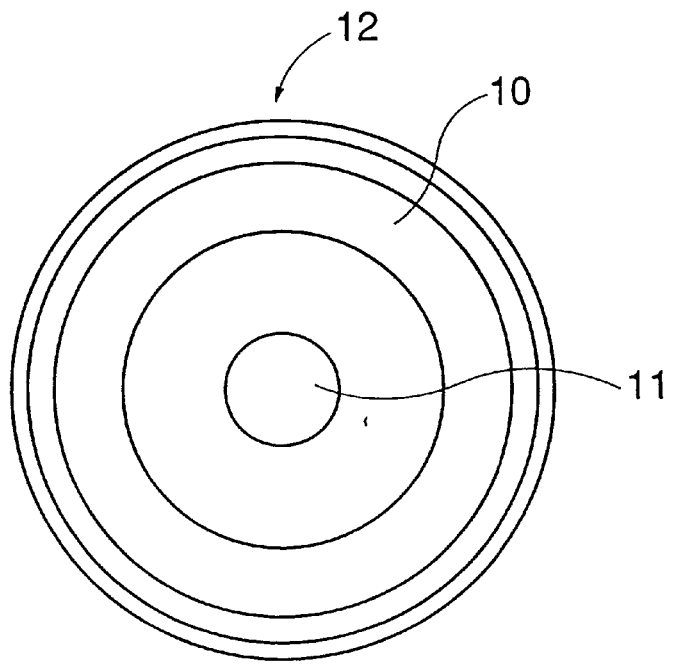
FIG. 3 is a front view showing an essential portion of FIG. 1.

Further, a condensing lens 9 is disposed at a light-incidence side of the through-bore 2, and a collimator lens 18 is disposed at a light-emitting side of the through-bore 2. A mirror 12 including a conical internal-reflection mirror section 10 and a conical external-reflection mirror section 11 as shown in FIG. 3 is disposed on the left end surface of the main body 1 shown in FIG. 1. The mirror 12 is fabricated by cutting an aluminum disk into a shape shown in FIGS. 1 and 3 and polishing its surface like a mirror, followed by vapor deposition of an Au film.

The coherence reducing element 3a is constructed with one multi-mode optical fiber 13 and protective metal collars 14, 15 mounted on both sides thereof, as shown in FIG. 1. A large-aperture optical fiber (MKH-08 type manufactured by Sumitomo Electric Industries, Ltd.) is used as the multi-mode optical fiber 13.

A pulse semiconductor laser (L4356-02 type manufactured by Hamamatsu Photonics K.K.) having a wavelength of 780 nm is used as the light source 7a; a pulse semiconductor laser (L4356-02 type manufactured by Hamamatsu Photonics K.K.) having a wavelength of 880 nm is used as the light sources 7b, 7d; and a red semiconductor laser (LT51 X D type manufactured by Sharp Corporation) having a wavelength of 635 nm is used as the light source 7c.

With this construction, a plurality of light beams emitted from the light sources 7a, 7b, 7c, 7d are converted into collimated light beams by the collimator lenses 8a, 8b, 8c, 8d, and reflected by the conical internal-reflection mirror section 10 of the mirror 12 in a direction perpendicular to the optical axis of the condensing lens 9 to be further reflected by the conical external-reflection mirror section 11 in a direction towards the condensing lens 9.

These light beams impinge into the condensing lens 9 in a state in which the light beams are equally spaced away from the optical axis of the condensing lens 9 at a predetermined distance. The light beams are then condensed by the condensing lens 9 to impinge into the light-receiving aperture of the coherence reducing element 3a respectively at the same predetermined angle of incidence. Here, since the optical path lengths from the light sources 7a, 7b, 7c, 7d to the condensing lens 9 are equal to each other, all the light beams are incident into the light-receiving aperture, with the same spot diameters.

The coherence reducing element 3a mixes the plurality of incident light beams, reduces the coherence of these light beams, flattens the light intensity distribution, and emits the light beams through an emitting aperture to the collimator lens 18. The collimator lens 18 converts the light beams from the coherence reducing element 3a into a collimated light beam having a single optical axis.

Here, the condensing lens 9 is set in such a manner that the incident angle of the light beams incident into the light-receiving aperture of the coherence reducing element 3a is smaller than the maximum incident angle defined by the numerical aperture of the light-receiving aperture, so as to prevent loss of light.

Also, the position relationship of the light-receiving aperture of the coherence reducing element 3a relative to the condensing lens 9 may be adjusted by adjusting the threads 5a, 5b to move an end portion of the coherence reducing element 3a that is protected by the metal collar 14, in a direction perpendicular to the central axis of the main body 1.

Thus, a collimated light beam with reduced coherence and flattened intensity distribution may be effectively obtained by using a plurality of laser light sources. In other words, the effects such as the following may be obtained.
(A) High uniformity of radiation intensity,
(B) High electro-optical energy conversion efficiency,
(C) Small size and small weight,
(D) Facility in handling emitted light, and
(E) High output stability and less change with time

SECOND EXAMPLE

Figure 4:
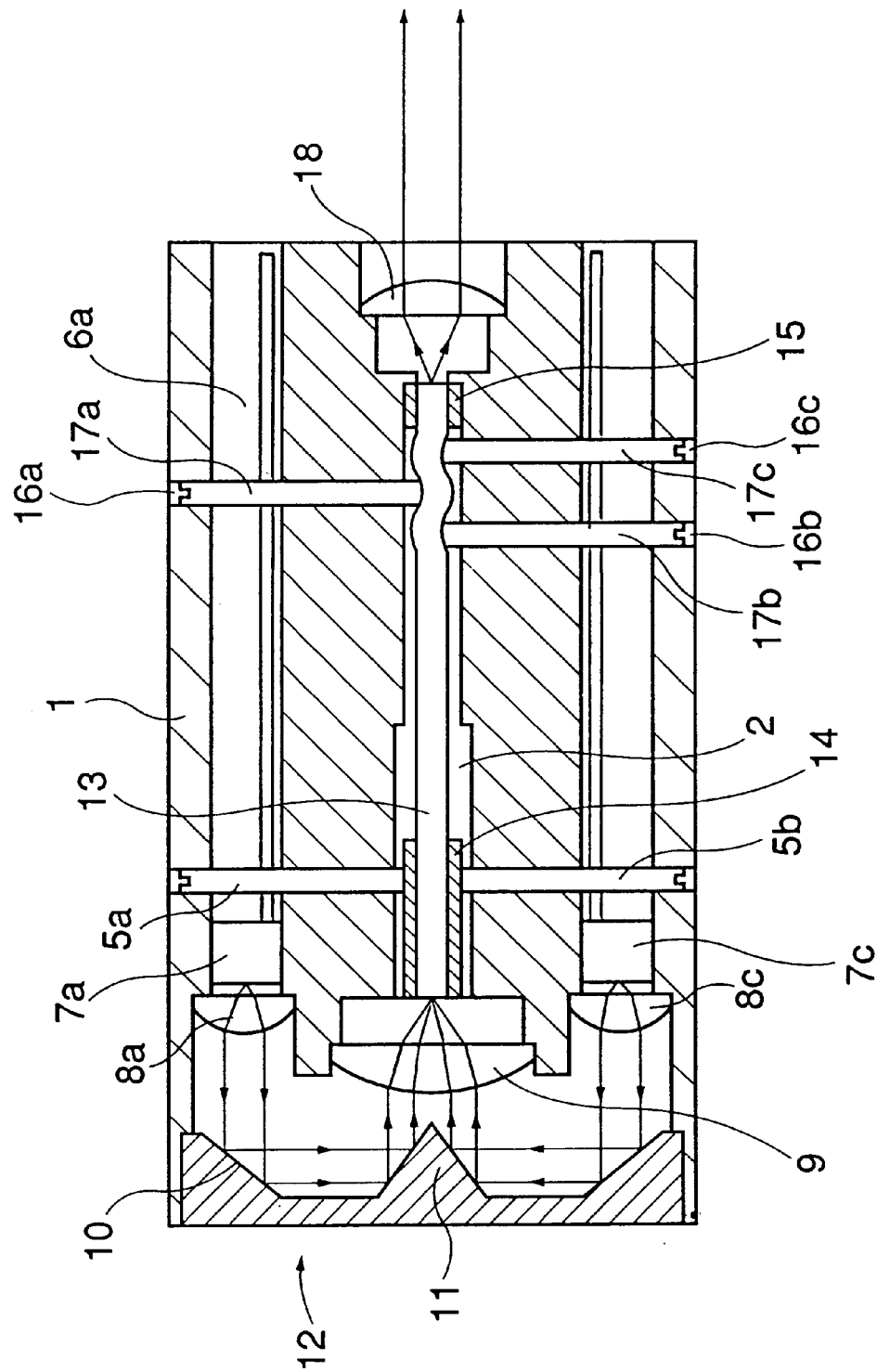
FIG. 4 is a cross-sectional view showing a construction of a second embodiment of a multiple light source unit according to the present invention.

FIG. 4 is a cross-sectional view showing a second embodiment of a multiple light source unit according to the present invention. Referring to FIG. 4, threads 17a, 17b, 17c are inserted into threadholes 16a, 16b, 16c formed upward and downward in the main body 1 in a direction perpendicular to the central axis of the main body 1. The threads 17a, 17b, 17c press a neighborhood of the emitting aperture of the multi-mode optical fiber 13 upward and downward into a W-shape. The other constituent elements are the same as in the first example (FIG. 1), and like numerals represent like elements in FIG. 1.

Generally, the number of stationary propagation modes and the propagation state of an optical fiber are determined by a wavelength and a core-clad refractive index. The light intensity distribution at the emitting aperture of the optical fiber is obtained by integration of peak intensities for the number of propagation modes, and assumes a discrete intensity distribution (sesame salt state). Therefore, by locally deforming the optical fiber as in this Example, a non-stationary propagation mode other than the stationary propagation modes is generated, thereby further flattening the distribution state of the light intensity.

THIRD EXAMPLE

Figure 5:
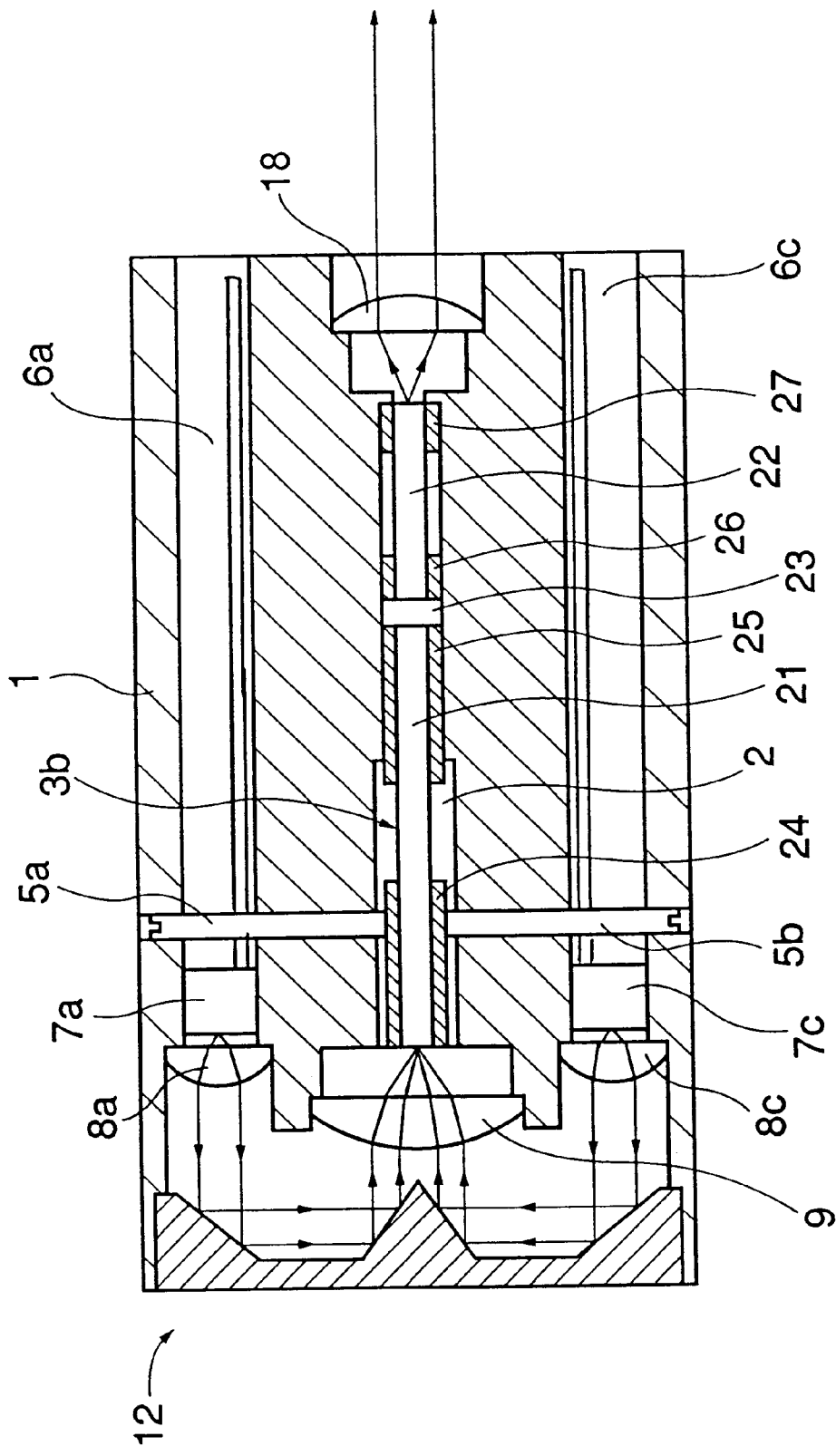
FIG. 5 is a cross-sectional view showing a construction of a third embodiment of a multiple light source unit according to the present invention.

FIG. 5 is a cross-sectional view showing a third embodiment of a multiple light source unit according to the present invention. In this Example, the coherence reducing element 3a of the first Example is replaced with a different coherence reducing element 3b, and the other constituent elements are the same as in the first Example (FIG. 1), so that explanation thereof will be omitted here.

The coherence reducing element 3b is constructed with two multi-mode optical fibers 21, 22 having different lengths, a light diffusing/scattering element 23 interposed therebetween, metal collars 24, 25 attached to both ends of the multi-mode optical fiber 21, and metal collars 26, 27 attached to both ends of the multi-mode optical fiber 22.

The multi-mode optical fiber 22 has a length shorter than the multi-mode optical fiber 21.

The light diffusing/scattering element 23 may be one of a holographic diffusing plate (manufactured by Material Technology Co., Ltd.), a holographic diffusing film (manufactured by NABA Co., Ltd.), and a homogenizer (manufactured by Optronics Co., Ltd.).

This construction allows the coherence reducing element 3b to generate a non-stationary propagation mode by means of the light diffusing/scattering element. Accordingly, the light intensity distribution is further flattened, as in the Example 2.

Here, the shorter multi-mode optical fiber 22 may be replaced with a metal pipe with a polished inner surface to form an optical guide path for guiding the non-stationary propagation mode.

FOURTH EXAMPLE

Figure 6:
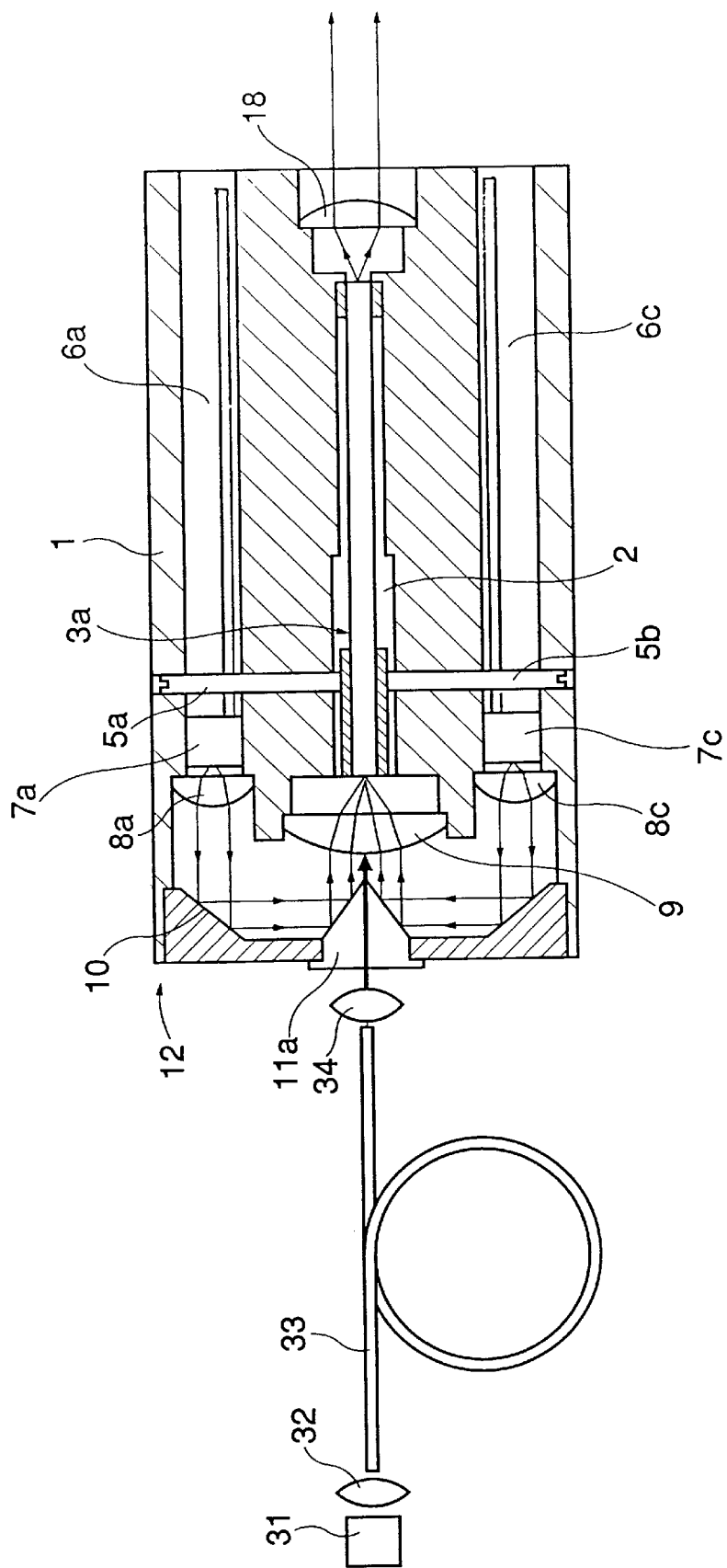
FIG. 6 is a cross-sectional view showing a construction of a fourth embodiment of a multiple light source unit according to the present invention.

FIG. 6 is a cross-sectional view showing a fourth embodiment of a multiple light source unit according to the present invention.

In this Example, the conical external-reflection mirror section 11 of the mirror 12 of the first Example is replaced with a different conical external-reflection mirror 11a, whereby a light beam from a light source 31 disposed outside of the main body 1 is incident via a condensing lens 32, an optical fiber 33, a collimator lens 34, and the conical external-reflection mirror 11a into the optical axis of the condensing lens 9. The other constituent elements are the same as in the first Example.

Here, the conical external-reflection mirror 11a has a dielectric film formed on a surface of an optically transparent material such as glass. The conical external-reflection mirror 11a transmits the light beam from the light source 31 and reflects the light beams from the light sources 8a, 8b, 8c, 8d in the same manner as the conical external-reflection mirror section 11 of the first Example.

This construction allows the light beam from the external light source 31 to be mixed together with the light beams from the light sources 8a, 8b, 8c, 8d by means of the coherence reducing element 3a, and the mixed light beams are emitted from the collimator lens 18 with a flattened light intensity distribution.

FIFTH EXAMPLE

Figure 7:
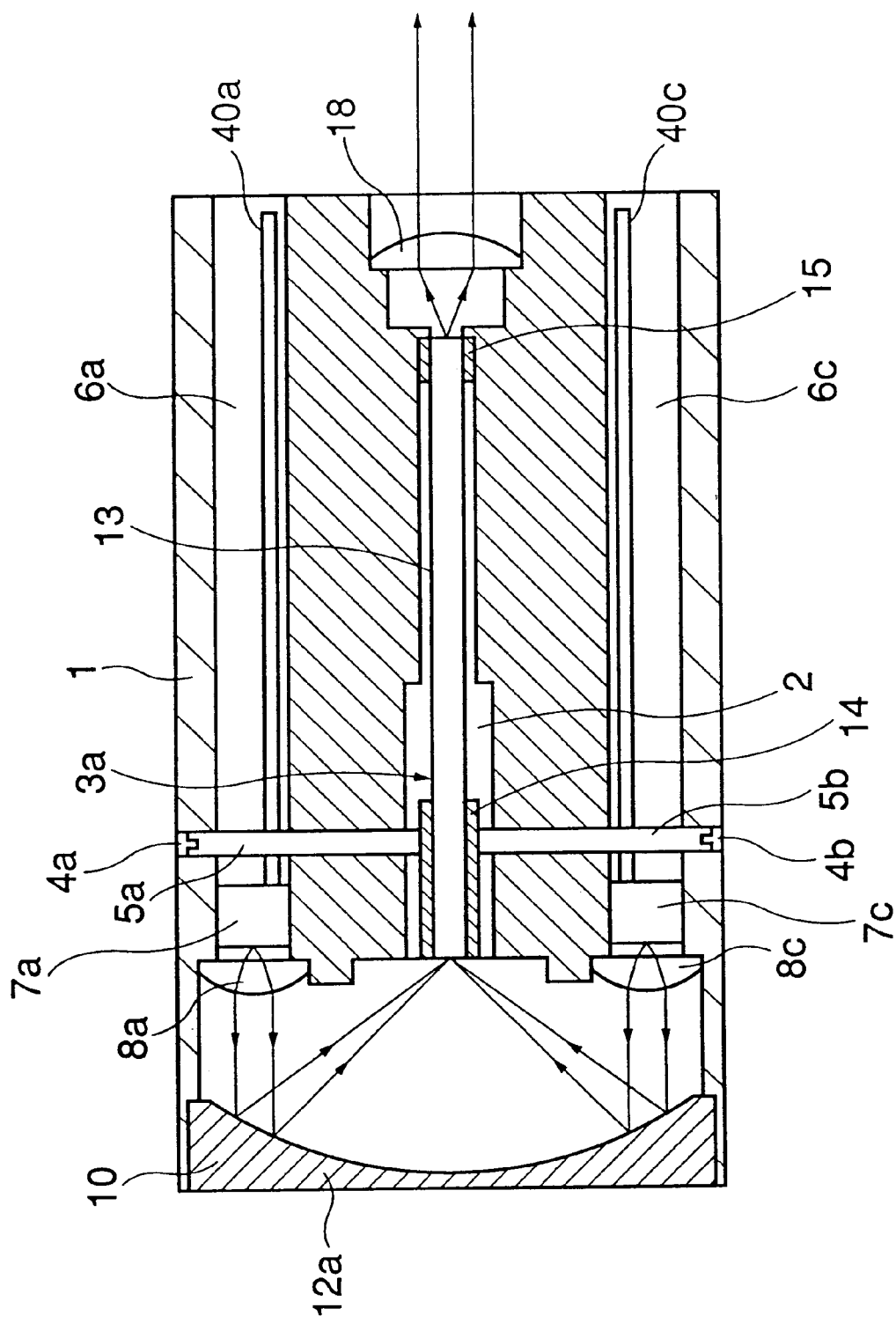
FIG. 7 is a cross-sectional view showing a construction of a fifth embodiment of a multiple light source unit according to the present invention.

FIG. 7 is a cross-sectional view showing a fifth embodiment of a multiple light source unit according to the present invention. In this Example, the mirror 12 and the condensing lens 9 of the first Example (FIG. 1) are replaced with a concave mirror 12a, and the other constituent elements are the same as in the first Example. Here, the coherence reducing element 3a is disposed in such a manner that its optical axis coincides with the optical axis of the concave mirror 12a and its light-receiving aperture is positioned at a focal point of the concave mirror 12a. The concave mirror 12a is fabricated by cutting an aluminum disk into a concave shape and polishing its surface like a mirror, followed by vapor deposition of an Au film.

With this construction, a plurality of light beams emitted from the light sources 7a, 7b, 7c, 7d are converted into light beams parallel to the optical axis of the concave mirror 12a by means of the collimator lenses 8a, 8b, 8c, 8d, and condensed by the concave mirror 12a to impinge into a light-receiving aperture of the coherence reducing element 3a at the same predetermined angle of incidence. Here, since the optical path lengths from the light sources 7a, 7b, 7c, 7d to the coherence reducing element 3a are equal to each other, all the light beams are incident into the light-receiving aperture, with the same spot diameters.

The coherence reducing element 3a mixes the plurality of incident light beams, reduces the coherence of these light beams, flattens the light intensity distribution, and emits the light beams through an emitting aperture to the collimator lens 18. The collimator lens 18 converts the light beams from the coherence reducing element 3a into a collimated light beam having a single optical axis.

Also, in the Examples 2 to 4, the mirror 12 and the condensing lens 9 may be replaced with a concave mirror 12a, as shown in FIG. 7.

SIXTH EXAMPLE

Figure 8:
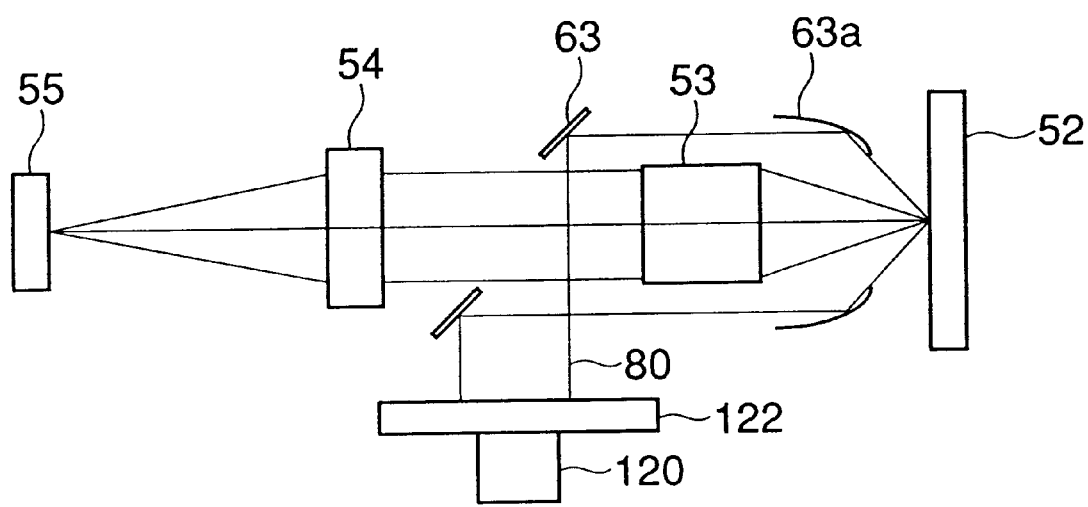
FIG. 8 is a view showing a fundamental construction of a sixth embodiment of the present invention.

FIG. 8 shows a fundamental construction of an optical system (image capturing device) utilizing any of the multiple light source units according to the first to fifth embodiments of the present invention. Referring to FIG. 8, a light beam emitted from a multiple light source unit 120 is converted into a light flux 80 having an annular cross section (i.e. a tubular light flux) by means of a light-flux producing section 122, and directed via a planar ring mirror 63 and an internal-reflection ring mirror 63a for irradiating an object 52 with dark field illumination. Optical information from the irradiated object 52 passes through a hollow space surrounded by the light flux 80 and directed via an object lens 53 and an imaging lens 54 to be focused on an image capturing element 55, which captures an image of the object 52.

Figure 9:
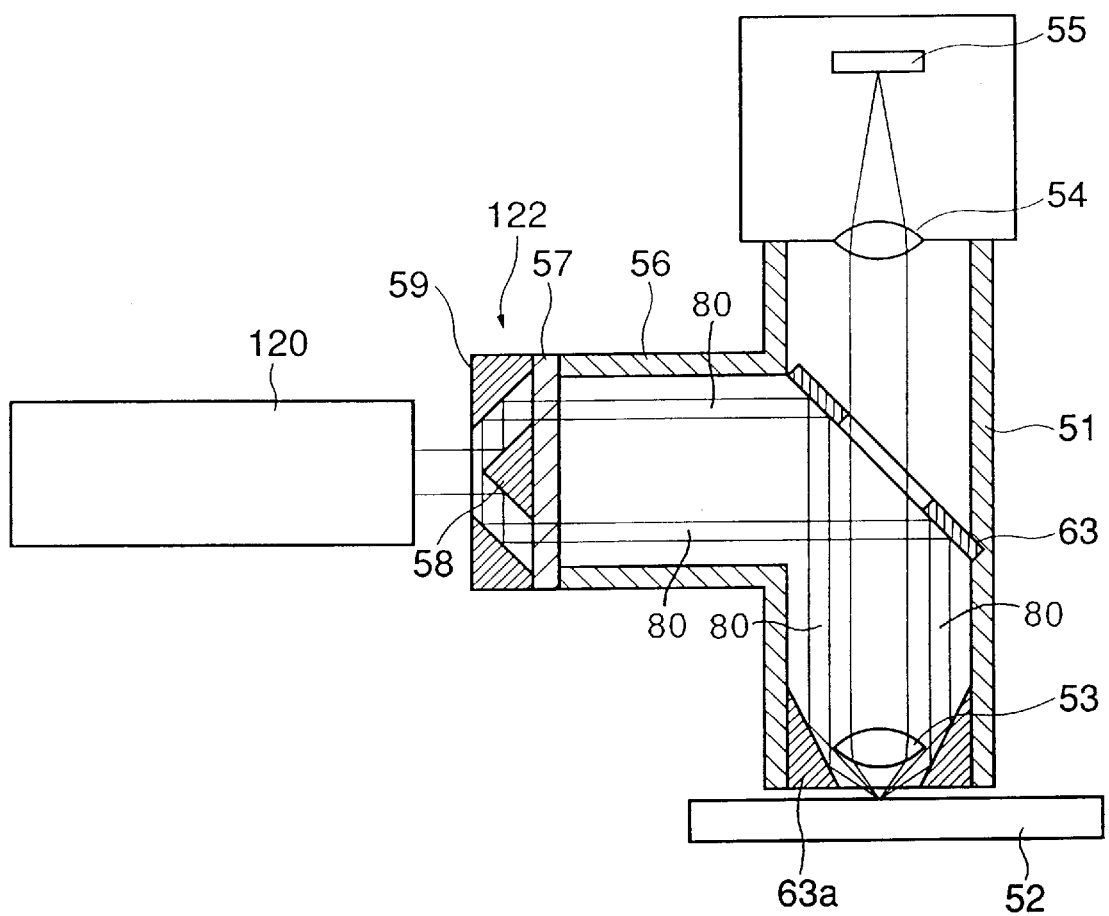
FIG. 9 is a view showing a concrete example of the sixth embodiment of the present invention.

FIG. 9 shows a practical image capturing device developed from the imaging device of FIG. 8.

Referring to FIG. 9, an object lens 53 and a conical internal-reflection mirror 63a surrounding the object lens 53 are disposed at the bottom of an image capturing tube 51 of an image capturing device, near an object 52 to be imaged. An imaging lens 54 and an image capturing element (for example, CCD) 55 are disposed at the top of the image capturing tube 51.

In addition, a light-flux producing section 122 is disposed at an end of an illuminating tube 56. The light-flux producing section 122 includes a disk-like light-transmitting plate 57. A conical reflection mirror 58 is fixed by adhesion to a central portion of an outer surface of the light-transmitting plate 57, and a conical internal-reflection mirror 59 is fixed by adhesion to a peripheral portion of the outer surface of the light-transmitting plate 57. A multiple light source unit 120 is disposed outside of the illuminating tube 56, and a planar ring mirror 63 is disposed at a central portion of the image capturing tube 51. Here, the multiple light source unit 120 may be any of the light source units fabricated according to the first to fifth Examples.

With this construction, a light beam emitted from the multiple light source unit 120 are reflected in a horizontal direction by both the conical reflection mirror 58 and the conical internal-reflection mirror 59 to be converted into a light flux 80 having an annular cross section. The light flux 80 then passes through the light-transmitting plate 57 to be reflected towards the object lens 53 by the planar ring mirror 63 and further reflected by the conical reflection mirror 63a for focusing on the object 52 from the outside of the object lens 53 to perform dark field illumination for the object 52.

Figure 10:
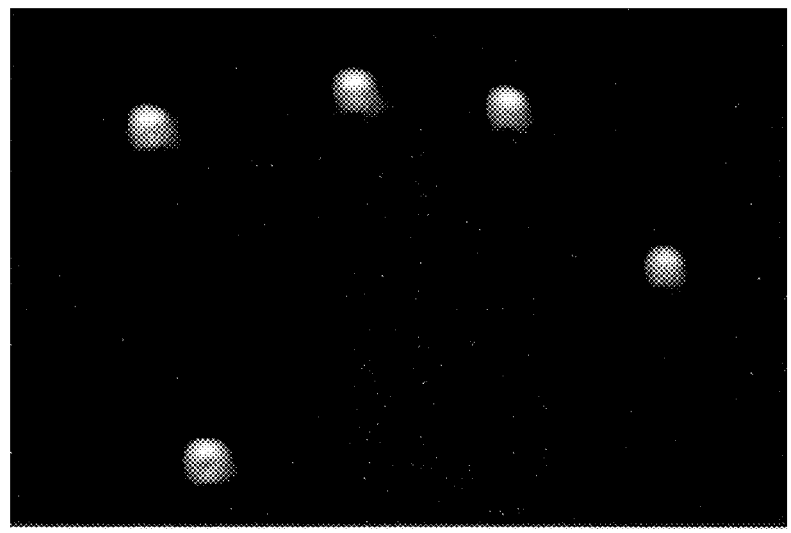
FIG. 10 is a view of an image (microscope photograph) captured according to the sixth embodiment of the present invention.
Figure 11:
FIG. 11 is a view of a comparative example (microscope photograph) in contrast with the sixth embodiment.

FIG. 10 shows an image actually obtained by capturing particles with a uniform particle size in this Example. FIG. 11 is an image (with the same magnification) obtained by replacing the multiple light source unit 120 with a conventional laser light source that does not include a coherence reducing element.

SEVENTH EXAMPLE

Figure 12:
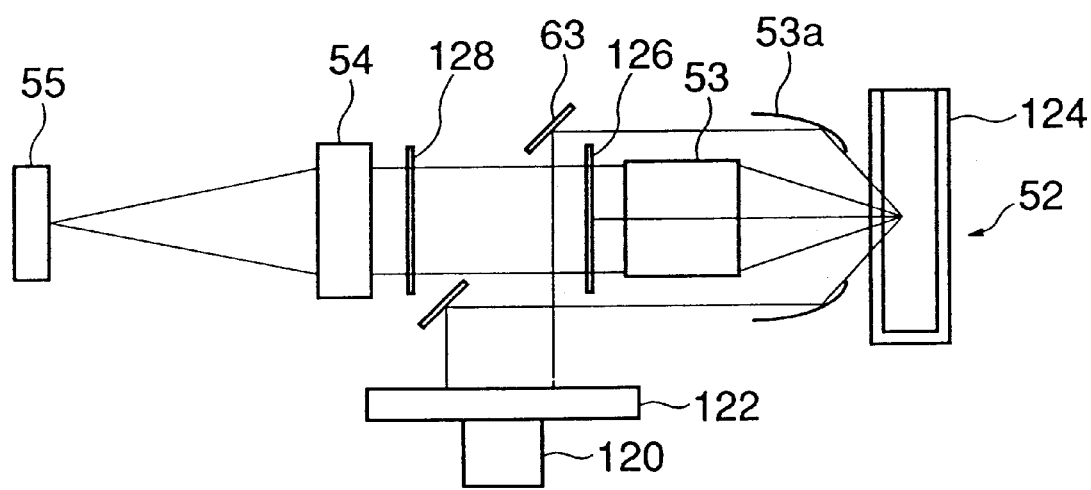
FIG. 12 is a view showing a fundamental construction of a seventh embodiment of the present invention.

FIG. 12 shows a basic construction of the seventh embodiment obtained by improving the image capturing device of the sixth embodiment. Spatial filters 126, 128 are coaxially disposed between an object lens 53 and an imaging lens 54. The other constituent elements are the same as in the sixth embodiment (FIG. 8). In the spatial filters 126, 128, a portion away from the optical axis has a high light transmittance than an optical axis portion. By using the spatial filters, the light beams of a specific angle among light beams emanating from the object 2 can be focused onto the image capturing element 55. This allows even an object in an optically scattering medium to be clearly imaged. In this Example, two imaging light beam limiting filters are used as the spatial filters 126, 128 in order to obtain a more preferable light beam limiting effect.

Figure 13:
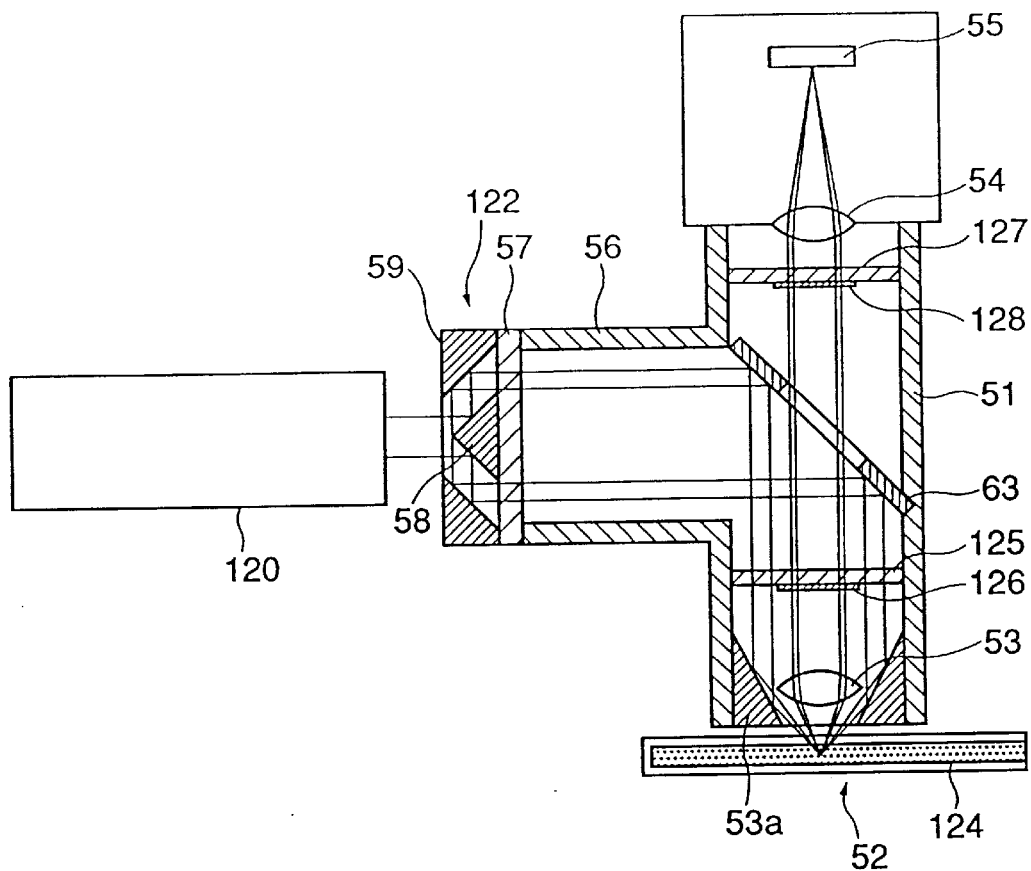
FIG. 13 is a view showing a concrete example of the seventh embodiment of the present invention.

FIG. 13 is an explanatory view showing a practical image capturing apparatus developed from the device of FIG. 12. The spatial filters, i.e. the imaging light beam limiting filters 126, 128 are fixed by adhesion to disk-like transparent glass plates 125, 127, respectively. The other constituent elements are the same as in the embodiment shown in FIG. 9.

Figure 14:
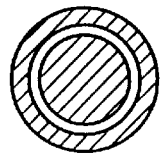
FIG. 14 is a front view of a spatial filter to be used in the seventh embodiment of the present invention.
Figure 15:
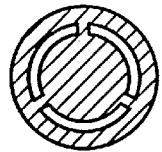
FIG. 15 is a front view of a spatial filter to be used in the seventh embodiment of the present invention.

FIG. 14 is a front view of the spatial filters 126, 128, which include an annular slit of 1 mm width located away from the optical axis by 5.5 mm for transmitting the light beams. In other words, these spatial filters 126, 128 are formed by bonding a thin copper plate ring having an outer diameter of 15 mm and an inner diameter of 12 mm and a thin copper disk having an outer diameter of 10 mm concentrically onto a transparent glass plate. Here, the annular slit of the spatial filters 126, 128 need not be a complete annulus, and a partially discontinuous annular slit such as shown in FIG. 15 produces similar effects.

Figure 16:
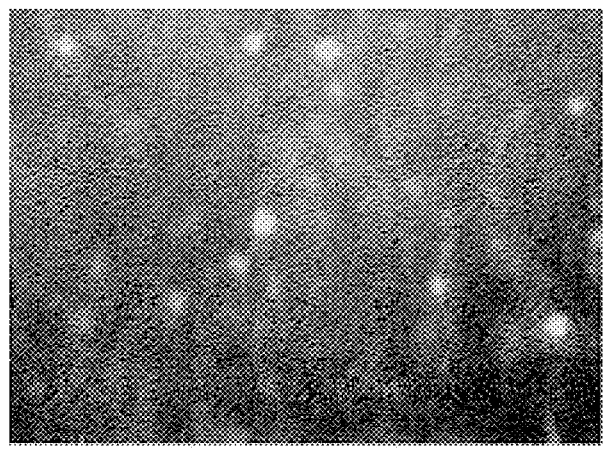
FIG. 16 is a view of an image (microscope photograph) captured according to the seventh embodiment of the present invention.
Figure 17:
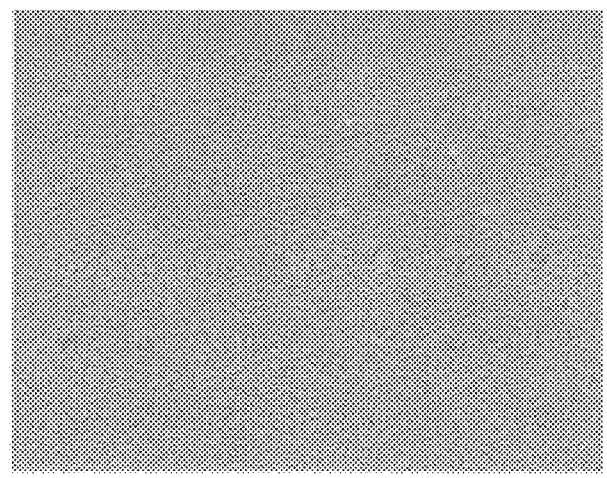
FIG. 17 is a view of a comparative example (microscope photograph) in contrast with the seventh embodiment.

FIG. 16 is an image captured by using an aqueous solution introduced into a hollow optical cell 124 having a square cross section of 10 mm×10 mm and containing fine particles of 5 $\mu$m diameter at several percent as an object 52 to be imaged, and by performing dark field illumination with red light of 638 nm wavelength from the light source unit 120. From FIG. 16, it will be understood that a clear image of the object (here, fine particles) in an optically scattering medium (for example, an aqueous solution) can be captured by using the spatial filters 126, 128. FIG. 17 shows an image of the object when the spatial filters 126, 128 are not used. In this case, an image of fine particles cannot be captured due to disturbance by optical scattering.

As shown and described above, the multiple light source unit of the present invention allows light beams from a plurality of light sources to be effectively incident into a light guiding element, whereby the plurality of light beams are mixed in the light guiding element to form a single light beam having a flattened intensity distribution. Accordingly, the effects such as the following may be obtained.

(A) High uniformity of radiation intensity,
(B) High electro-optical energy conversion efficiency,
(C) Small size and small weight,
(D) Facility in handling emitted light, and
(E) High output stability and less change with time According to the optical system of the present invention, a clear image may be obtained without interference fringes, Fresnel diffraction, or Fraunhofer diffraction.

Although the present invention has fully been described by way of example with reference to the accompanying drawings, it is to be understood that various changes and modifications will be apparent to those skilled in the art. Therefore, unless otherwise such changes and modifications depart from the scope of the invention, they should be construed as being included therein.

What we claim is:

1. A multiple light source unit comprising:
   a plurality of light sources for emitting light beams;
   a condensing lens, the light beams being parallel to an optical axis of the condensing lens;
   a mirror for directing the light beams from the plurality of light sources to the condensing lens; and
   a light guiding element for receiving the condensed light beams through a light receiving section and for emitting the light beams through a light emitting section,
   wherein the light beams from the plurality of light sources are incident, through respective positions on the condensing lens, into the light receiving section of the light guiding element.

2. The multiple light source unit according to clam 1, wherein the plurality of light sources are spaced apart on a circumference coaxial with the optical axis of the condensing lens.

3. The multiple light source unit according to claim 1, wherein the plurality of light sources include a laser light source and the light guiding element includes a coherence reducing element for reducing a coherence of the received light beams.

4. The multiple light source unit according to claim 1, further comprising an adjusting section for adjusting a position relationship of the light receiving section of the light guiding element relative to the condensing lens.

5. The multiple light source unit according to claim 1, wherein the plurality of light sources are spaced apart on a circumference coaxial with an optical axis of the condensing lens;
   the mirror comprises a first mirror and a second mirror, the first mirror reflecting the light beams from the light sources in a direction that intersects the optical axis of the condensing lens, the second mirror allowing the light beams reflected from the first mirror to be incident into the condensing lens by directing the light beams in a direction parallel to the optical axis of the condensing lens; and
   the first mirror is a conical internal-reflection mirror for reflecting the light beams from the plurality of light sources, and the second mirror is a conical external-reflection mirror for reflecting the light beams from the first mirror.

6. The multiple light source unit according to claim 5, further comprising an auxiliary light source for emitting a collimated light beam, wherein the conical external-reflection mirror is configured to emit, from an apex thereof, the light beam incident into a bottom thereof, whereby light beam from the auxiliary light source passes through the bottom and through the apex of the conical external-reflection mirror to be incident into the optical axis of the condensing lens.

7. An optical system comprising:
   a light-flux producing section for converting the light emitted from a multiple light source unit of claim 1, into a light flux having an annular cross section;
   an internal-reflection mirror for condensing the light flux onto an object for radiation;
   an object lens for receiving the light from the radiated object through a hollow space surrounded by the light flux;
   an imaging lens disposed on an optical axis of the object lens; and
   an image capturing element for capturing an image formed by the imaging lens.

8. A multiple light source unit comprising:
   a plurality of light sources for emitting light beams;
   a mirror for reflecting and condensing the light beams from the plurality of light sources; and
   a light guiding element located in a bore of a main body for receiving the condensed light beams through a light receiving section and for emitting the light beams through a light emitting section,
   wherein the light beams from the plurality of light sources are incident, through respective positions on the mirror, into the light receiving section of the light guiding element.

9. The multiple light source unit according to claim 8, wherein the plurality of light sources include a laser light source and the light guiding element includes a coherence reducing element for reducing a coherence of the received light beams.

10. The multiple light source unit according to claim 8, wherein the plurality of light sources are spaced apart on a circumference coaxial with the optical axis of the mirror; the light guiding element has an optical axis that coincides with the optical axis of the mirror; and the light receiving section is positioned at a focal point of the concave mirror.

11. The multiple light source according to claim 8, wherein the mirror includes a concave mirror.

12. The multiple light source unit according to claim 8, wherein the plurality of light sources are spaced apart on a circumference coaxial with the optical axis of the mirror.

13. The multiple light source unit according to claim 8, wherein the mirror is aluminum with a gold coating.

14. An optical system comprising:
   a light-flux producing section for converting the light emitted from a multiple light source unit, into a light flux having an annular cross section;
   a plurality of light sources for emitting light beams;
   a mirror for reflecting and condensing the light beams from the plurality of light sources; and
   a light guiding element for receiving the condensed light beams through a light receiving section and for emitting the light beams through a light emitting section,
   wherein the light beams from the plurality of light sources are incident, through respective positions on the mirror, into the light receiving section of the light guiding element,
   an internal-reflection mirror for condensing the light flux onto an object for radiation;
   an object lens for receiving the light from the radiated object through a hollow space surrounded by the light flux;
   an imaging lens disposed on an optical axis of the object lens; and
   an image capturing element for capturing an image formed by the imaging lens.

15. The multiple light source unit according to claim 1, wherein the mirror is aluminum with a gold coating.

* * * * *